United States Patent
Takai

(10) Patent No.: US 7,853,059 B2
(45) Date of Patent: Dec. 14, 2010

(54) MAGNETIC RESONANCE IMAGING APPARATUS, METHOD OF MAKING AN IMAGING-PLAN, AND METHOD OF IMAGING

(75) Inventor: Hiroshi Takai, Yaita (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 1021 days.

(21) Appl. No.: 11/605,319

(22) Filed: Nov. 29, 2006

(65) Prior Publication Data

US 2007/0122019 A1 May 31, 2007

(30) Foreign Application Priority Data

Nov. 30, 2005 (JP) .............................. 2005-347175

(51) Int. Cl.
*G06K 9/00* (2006.01)
*A61B 5/05* (2006.01)

(52) U.S. Cl. ...................................... 382/128; 600/410
(58) Field of Classification Search ................ 382/128, 382/129, 130, 131, 132, 133, 134; 378/4, 378/21–27, 113, 901; 600/407, 410, 425, 600/427, 524; 128/920, 922; 424/9.3; 430/39; 436/173
See application file for complete search history.

(56) References Cited

U.S. PATENT DOCUMENTS

| | | | | |
|---|---|---|---|---|
| 5,699,799 A | * | 12/1997 | Xu et al. | 600/407 |
| 6,540,679 B2 | * | 4/2003 | Slayton et al. | 600/439 |
| 6,608,916 B1 | * | 8/2003 | Wei et al. | 382/132 |
| 6,764,217 B2 | * | 7/2004 | Yasuda et al. | 378/205 |

FOREIGN PATENT DOCUMENTS

| JP | 7-51248 | 2/1995 |
|---|---|---|
| JP | 8-289888 | 11/1996 |
| JP | 2003-210430 | 7/2003 |

* cited by examiner

*Primary Examiner*—Abolfazl Tabatabai
(74) *Attorney, Agent, or Firm*—Nixon & Vanderhye PC

(57) ABSTRACT

The present invention provides a magnetic resonance imaging apparatus including a unit for specifying a plurality of regions of interest on a plurality of original images acquired by imaging several times while shifting imaging positions, a unit for finding an approximate line involved in the regions of interest on an image formed by combining the original images, and a determining unit for determining conditions required to image cross sections crossing the original images on the basis of the approximate line.

20 Claims, 9 Drawing Sheets

MAGNETIC RESONANCE IMAGING APPARATUS, METHOD OF MAKING AN IMAGING-PLAN, AND METHOD OF IMAGING

CROSS-REFERENCE TO RELATED APPLICATIONS

This application is based upon and claims the benefit of priority from prior Japanese Patent Application No. 2005-347175, filed Nov. 30, 2005, the entire contents of which are incorporated herein by reference.

BACKGROUND OF THE INVENTION

1. Field of the Invention

The present invention relates to a magnetic resonance imaging apparatus that images a wide area by imaging an object several times while changing imaging positions, a method of making an imaging-plan for the magnetic resonance imaging apparatus, and an imaging method that is performed by the magnetic resonance imaging apparatus.

2. Description of the Related Art

In recent years, a method of imaging a wide area (hereafter, called wide-area imaging), which can not be imaged at one time, by imaging the area several times while moving a bed is used. Uses of the wide-area imaging considered now are as follows.

(1) Metasearch of the whole body: STIR-T2, angiography, and DWI.

(2) in the case of finding that metastasis has spread, as a result of scanning for target regions.

liver: same as the metasearch, when finding something in the liver and intending to image other regions: STIR and DWI.

spine: After imaging meta of the lumbar, when intending to image the cervical vertebrae: STIR-T2 and angiography.

Syringomyelia is the same as the above.

aortic aneurysm: when intending to image the pelvis.

(3) As for mass lesion of the pelvis.

When intending to image a desired region deviating from a Z direction, because a volume exists in the Z direction.

(4) Examination of an abdomen of person with large body frame.

(5) Blood vessel image of the brachium (from the ends of the fingers to the shoulder).

(6) Imaging the whole spine including the medullar.

An automatic imaging-plan for the spine image is disclosed in U.S. Pat. No. 6,608,916. A method of automatically determining slice positions of interspinal disc is disclosed in JP-A No. 7-51248. A method of making an imaging-plan for a magnetic field resonance imaging apparatus is disclosed in JP-A No. 2003-210430. Further, a method of making an imaging-plan including a plurality of target objects is disclosed in JP-A No. 11-113876.

However, in wide-area imaging, as described in the related art, in addition to consideration to determination of positions with respect to regions of interest or selection of FOV (field of view) without return, it is required to consider continuity of slices imaged and spatial resolution, so that it takes considerable time and effort to make an imaging-plan.

BRIEF SUMMARY OF THE INVENTION

A method of easily making an imaging-plan is required in consideration of the above problems.

A magnetic resonance imaging apparatus according to an first aspect of the invention includes a unit for specifying a plurality of regions of interest on a plurality of original images acquired by imaging several times while shifting imaging positions, a unit for finding an approximate line involved in the regions of interest on an image formed by combining the original images, and a determining unit for determining conditions required to image cross sections crossing the original images on the basis of the approximate line.

A magnetic resonance imaging apparatus according to a second aspect of the invention includes an imaging unit for generating magnetic resonance signals by applying gradient magnetic fields and high frequency pulses to an object in a static magnetic field, a bed for longitudinally sliding a top board with an object placed, a high frequency coil for detecting the magnetic resonance signals, a display unit for displaying positioning images, a specifying unit specifying a plurality of regions of interest according to specifying order of an operator on the positioning images, a calculating unit calculating coverage surrounding a plurality of regions of interest depending on the regions of interest specified by the specifying unit, a changing unit changing the coverage according to changing order of the operator, and a control unit controlling the imaging unit, the bed, and the high frequency coils to image cross sections, several times while shifting imaging positions, which is formed by the coverage crossing the positioning image when the coverage defined by confirmation about the conditions of the operator is larger than a region defined by the static magnetic field and can be imaged.

A method of making an imaging-plan according to a third aspect of the invention includes specifying a plurality of regions of interest on a plurality of original images acquired by imaging several times while shifting imaging positions, finding an approximate line involved in the regions of interest on an image formed by combining the original images, and determining conditions for imaging cross sections crossing the original images on the basis of an approximate line.

A method of imaging according to a fourth aspect of the invention includes specifying a plurality of regions of interest according to specifying order of an operator on the positioning images, calculating coverage surrounding a plurality of regions of interest depending on the regions of interest specified by the specifying unit, changing the coverage according to changing order of the operator, and controlling the imaging unit, the bed, and the high frequency coil to image cross sections, several times while shifting imaging positions, which is formed by the coverage crossing the positioning image when the coverage defined by confirmation about the conditions of the operator is larger than a region defined by the static magnetic field and can be imaged.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Preferred embodiments of the invention are described in detail hereafter with reference to the accompanying drawings.

Figure 1:
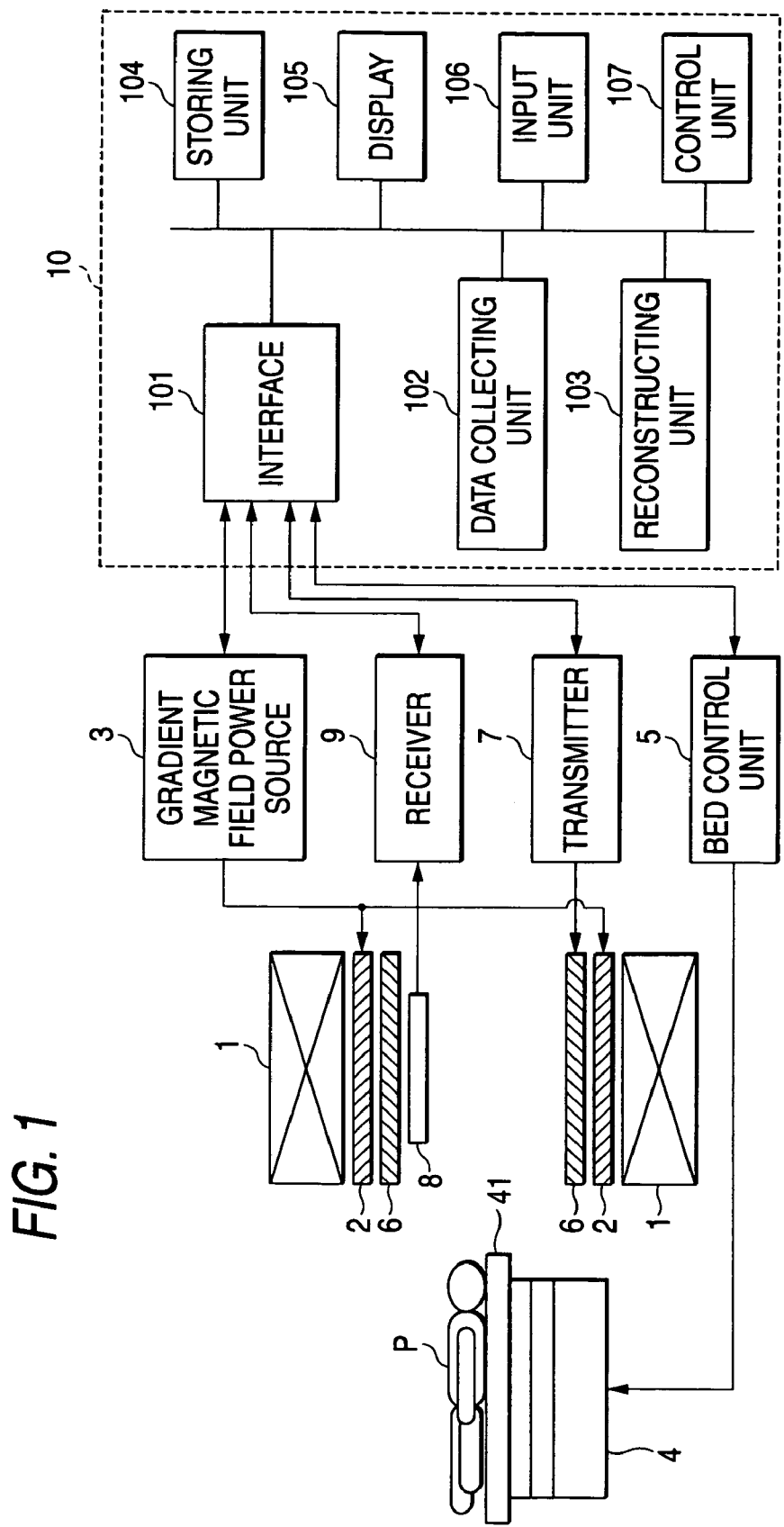
FIG. 1 is a view illustrating a configuration of a magnetic resonance imaging apparatus (MRI apparatus) according to an embodiment of the invention.

FIG. 1 is a view illustrating a configuration of a magnetic resonance imaging apparatus (MRI apparatus) according to an embodiment of the invention. The MRI apparatus shown in FIG. 1 includes a static magnetic field magnet 1, a gradient magnetic field coil 2, a gradient magnetic field power source 3, a bed 4, a bed control unit 5, a transmission RF coil 6, a transmitter 7, a reception RF coil 8, a receiver 9, and a calculator system 10.

The static magnetic field magnet 1 has a hollow cylinder shape and generates a homogeneous static magnetic field inside the cylinder. For example, a permanent magnet or a superconductive magnet may be used for the static magnetic field magnet 1.

The gradient magnetic field coil 2 has a hollow cylindrical shape and is disposed inside the static magnetic field magnet 1. The gradient magnetic field coil 2 is configured by three coils corresponding to X-axis, Y-axis, and Z-axis which are perpendicular to each other. The three coils of the gradient magnetic field coil 2 are respectively supplied with currents from the gradient magnetic field power source 3 and generate gradient magnetic fields whose intensities are inclined along the X-axis, the Y-axis, and the Z-axis. The Z-axis direction is, for example, the same as that of the static magnetic field. The gradient magnetic fields of the X-axis, the Y-axis, and the Z-axis respectively correspond to, for example, a gradient magnetic field Gs for selecting slice, a gradient magnetic field Ge for phase encode, and a gradient magnetic field Gr for read-out. The gradient magnetic field Gs for selecting slice is used to arbitrarily determine imaging cross sections. The gradient magnetic field Ge for phase encode is used to encode phases of magnetic resonance signals on the basis of spatial positions. The gradient magnetic field Gr for read-out is used to encode frequencies of magnetic resonance signals on the basis of spatial positions.

An object P to be examined that is disposed on a top board 41 of the bed 4 is inserted into a hollow (imaging inlet) of the gradient coil 2. The top board 41 of the bed 4 is driven by the bed control unit 5 and moves in a longitudinal direction and a vertical direction. In general, the bed 4 is disposed such that its longitudinal direction is parallel to the center axis of the static magnetic field magnet 1.

The transmission RF coil 6 is disposed inside the gradient magnetic field coil 2. The transmission RF coil 6 receives high frequency pulses from the transmitter 7 and then generates a high frequency magnetic field.

The transmitter 7 includes an oscillator, a phase selector, a frequency converter, an amplitude modulator, and a high frequency electric power amplifier that are mounted therein. The oscillator generates and transmits high frequency signals with natural resonance frequencies to desired atom nuclei in the static magnetic field. The phase selector selects phases of the high frequency signals. The frequency converter converts the frequencies of the high frequency signals outputted from the phase selector. The amplitude modulator modulates amplitudes of the high frequency signals outputted from the frequency converter, for example, by employing a sink function. The high frequency electric power amplifier amplifies the high frequency signals outputted from the amplitude modulator. As a result of operations of these parts, the transmitter 7 transmits high frequency pulses corresponding to Larmor frequencies to the transmission RF coil 6.

The reception RF coil 8 is disposed inside the gradient magnetic field coil 2. The reception RF coil 8 receives magnetic resonance signals that are transferred from an object due to influence by the high frequency magnetic field. Signals outputted from the reception RF coil 8 are inputted into the receiver 9.

The receiver 9 creates magnetic resonance signal data on the basis of the output signals from the reception RF coil 8.

The calculator system 10 includes an interface 101, a data collecting unit 102, a reconstructing unit 103, a storing unit 104, a display 105, an input unit 106, and a control unit 107.

The gradient magnetic field power source 3, the bed control unit 5, the transmitter 7, the reception RF coil 8, and the receiver 9 are connected to the interface 101. The interface 101 inputs and outputs signals transferred between each of the connected components and the calculator system 10.

The data collecting unit 102 collects digital signals outputted from the receiver 9 through the interface 101. The data collecting unit 102 stores the collected digital signals, i.e. magnetic resonance signal data in the storing unit 104.

The reconstructing unit 103 applies post-process, i.e. Fourier Transform and the like, to the magnetic resonance signal data stored in the storing unit 104 to reconstruct the data, and acquires spectrum data or image data of spin of the desired nuclei in an object P.

The storing unit 104 stores the magnetic resonance signal data and spectrum data or image data for each patient.

The display 105 displays a variety of information of the spectrum data, image data, etc. under the control by the control unit 107. Display devices, such as liquid crystal displays, may be used for the display 105.

The input unit 106 receives a variety of orders and information from an operator. Pointing devices, such as a mouse or a trackball, selecting devices, such as a mode shifting switch, or input devices, such as a keyboard, may be used for the input unit 106.

The control unit 107 inclusively controls the MRI apparatus according to the present embodiment by using a CPU or memories (not shown) etc. In addition to the control functions of an MRI apparatus for normal operations, the control unit 107 has functions allowing processes (described later) to support in making an imaging-plan.

The operation of an MRI apparatus configured as described above will now be described hereafter.

Further, by using a total spine imaging method in which the wide area imaging method is frequently used, as an example, the processes for making an imaging-plan are described below with reference to a coronal image (that perpendicular coronals are oblique) that is scanned three times using sagittal images as the original images. The original images are also scanned three times and three original images are prepared.

Figure 2:
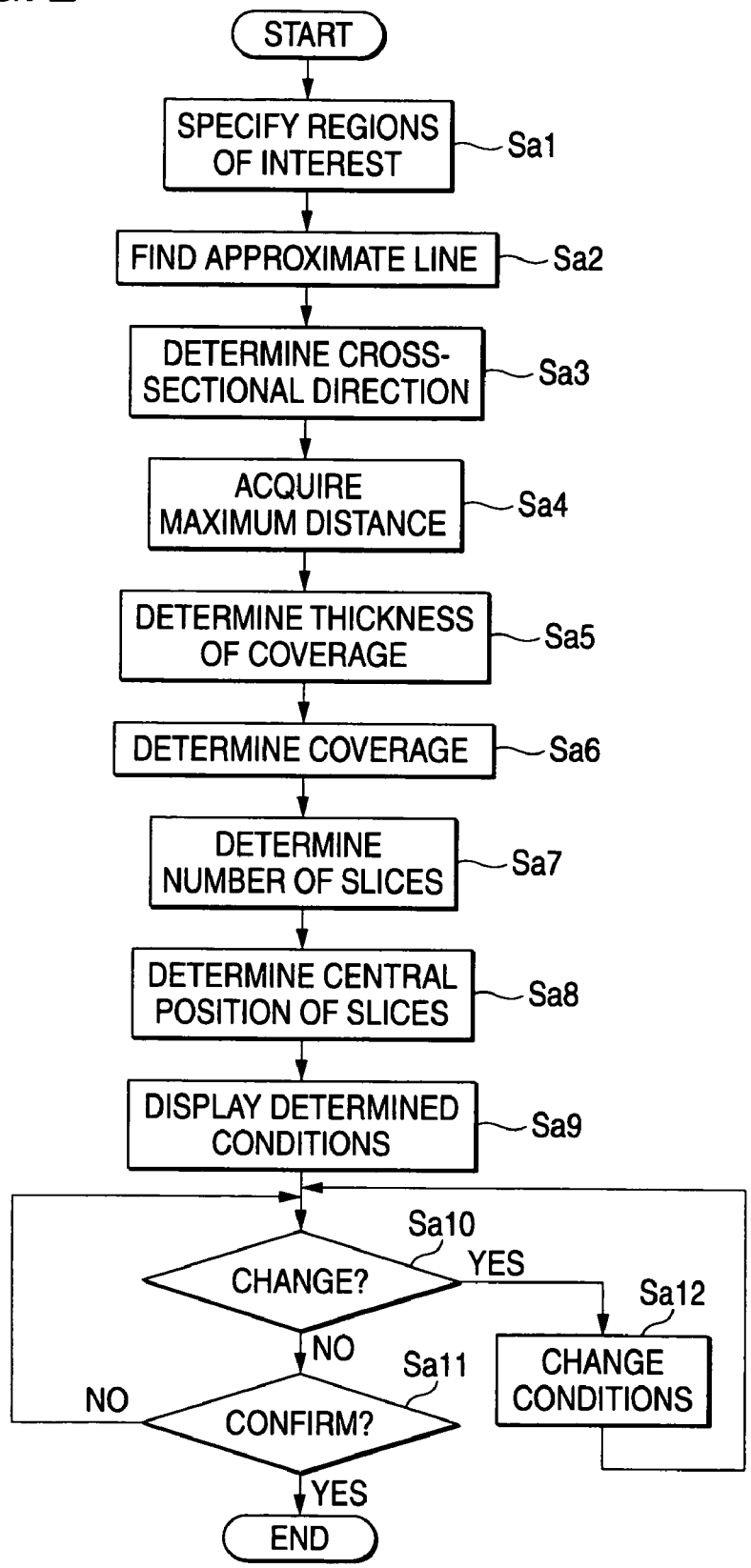
FIG. 2 is a flowchart illustrating a processing order in a control unit for supporting the determination of imaging conditions for imaging-plan of FIG. 1.

FIG. 2 is a flowchart illustrating a processing order in a control unit 107 for supporting setting of imaging conditions for an imaging-plan of FIG. 1.

In step Sa1, the control unit 107 specifies a plurality of regions of interest, for example, on the basis of orders of an operator. Regions of interest may be specified by using a mouse or a numerical keypad, or names, for example, 'a fifth cervical vertebra'. It is preferable to specify regions of interest for all original images.

Figure 3A:
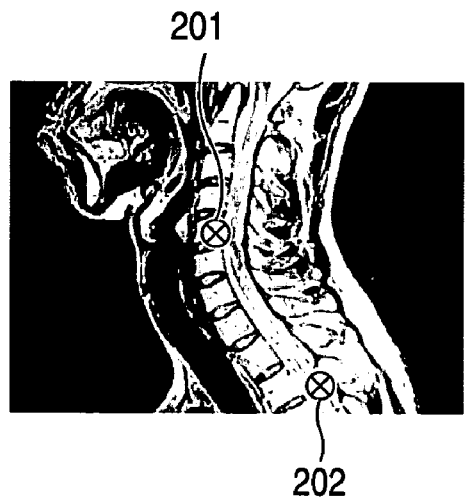
FIGS. 3A, 3B, and 3C are views illustrating examples for three original images.
Figure 3B:
Figure 3C:
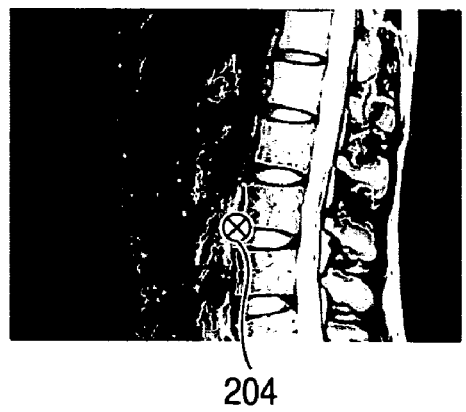

FIGS. 3A to 3C illustrate examples for three original images. As regions to mainly image, the spine is shown in FIG. 3A, the dorsal spine is shown in FIG. 3B, and the lumbar is shown in FIG. 3c. Because the original images are obtained by collecting MR signals while moving each region of interest to the center of the magnetic field, corrugation caused by inhomogeneities of the static magnetic field or gradient magnetic fields is small and the resolution is improved. In FIGS. 3A to 3C, four regions of interest 201 to 204 are indicated by an X mark. Such regions of interest are primarily selected from the centrum, the disc, or the spine.

Figure 4:
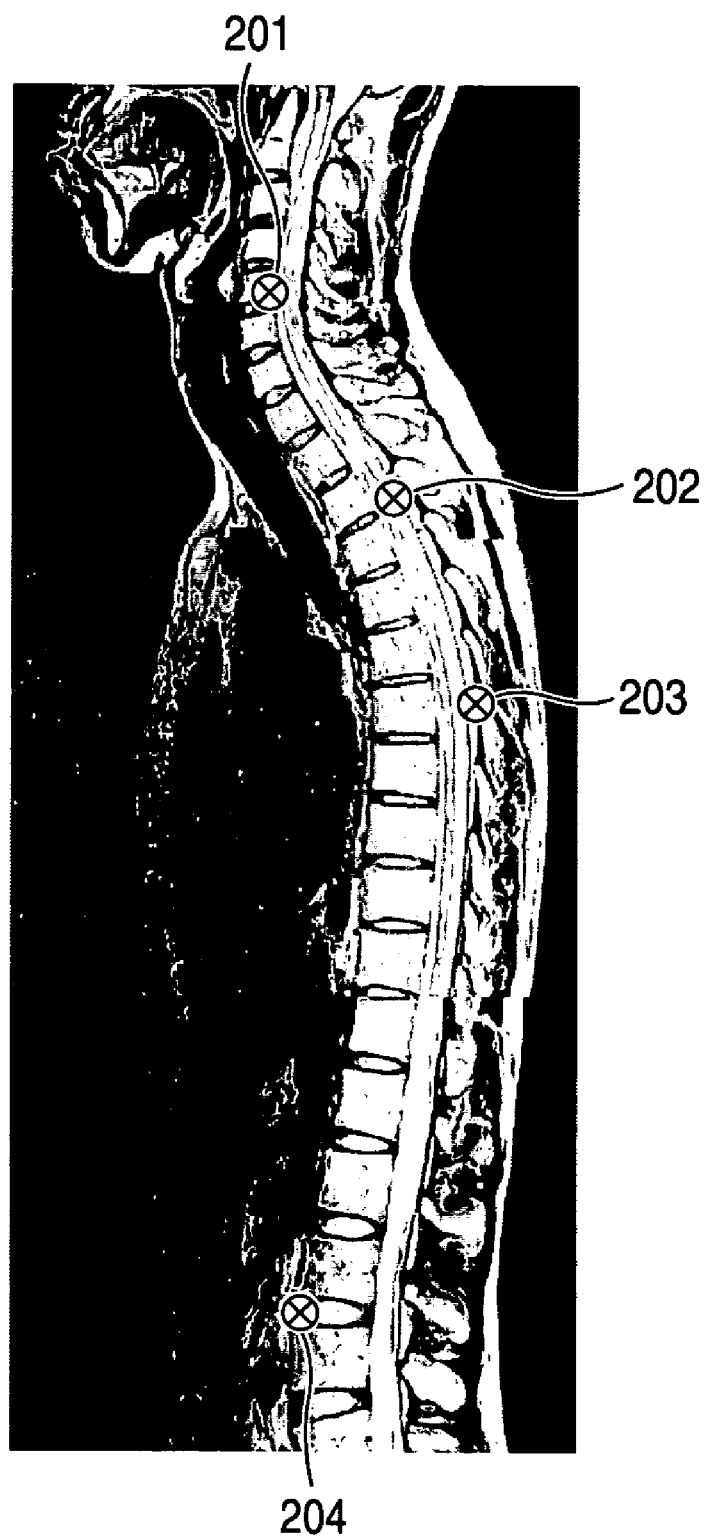
FIG. 4 is a view illustrating regions of interest shown on an image formed by combining the three original images of FIGS. 3A, 3B, and 3C on the basis of positional information in a patient coordinate system.

FIG. 4 is a view illustrating regions of interest shown on an image formed by combining the three original images on the basis of positional information in a patient coordinate system. It is preferable to specify the regions of interest on the combined image.

Figure 5:
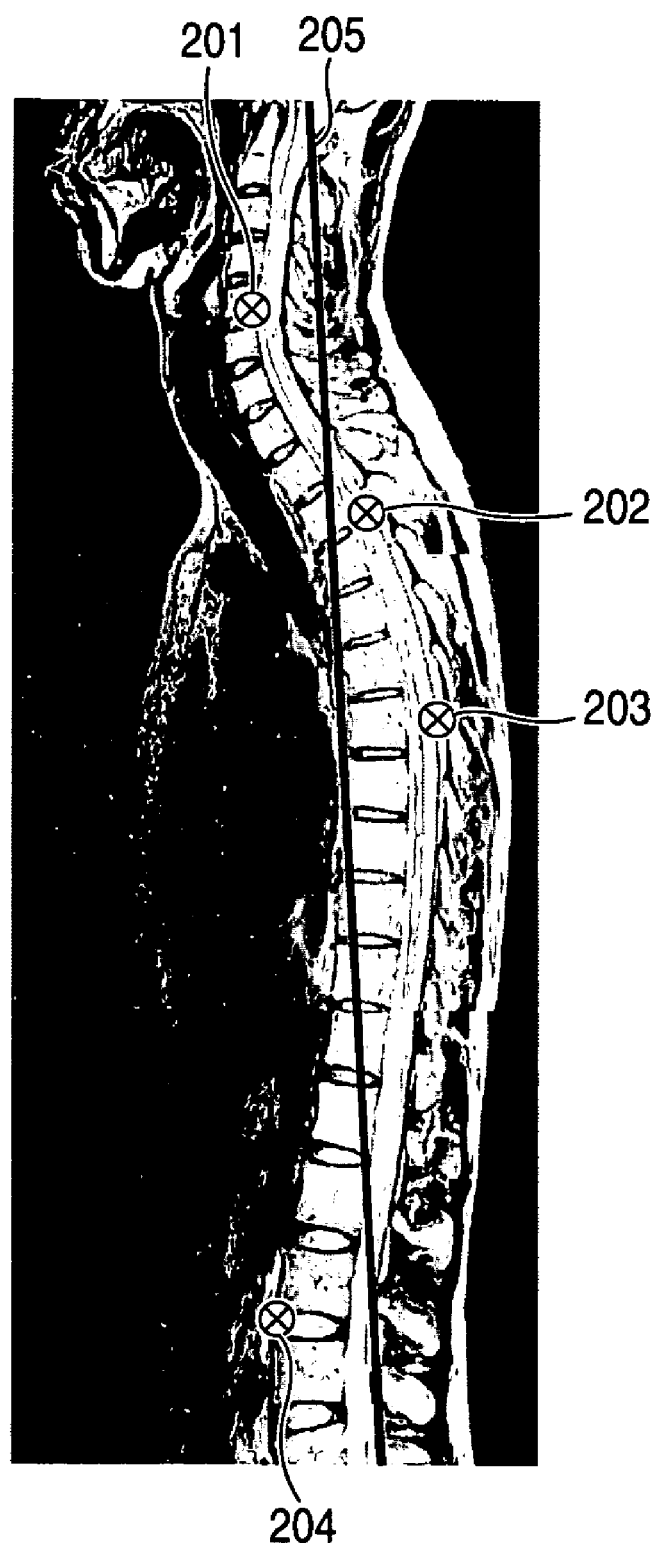
FIG. 5 is a view illustrating an approximate line 205 acquired from relationships of four regions of interest shown in FIG. 4.

In step Sa2, the control unit 107 determines an approximate line by applying linear regression to positional coordinates of the regions of interest in a patient coordinate system employing a method of least squares. FIG. 5 shows an approximate line 205 for the regions of interest 201 to 204. In step Sa3, the control unit 107 determines a cross-sectional direction parallel to that of the approximate line 205. However, a point specified on a slice other than the approximate line 205 and the original image may be a slice surface and the cross-sectional direction may be parallel to that of the slice surface.

Figure 6:
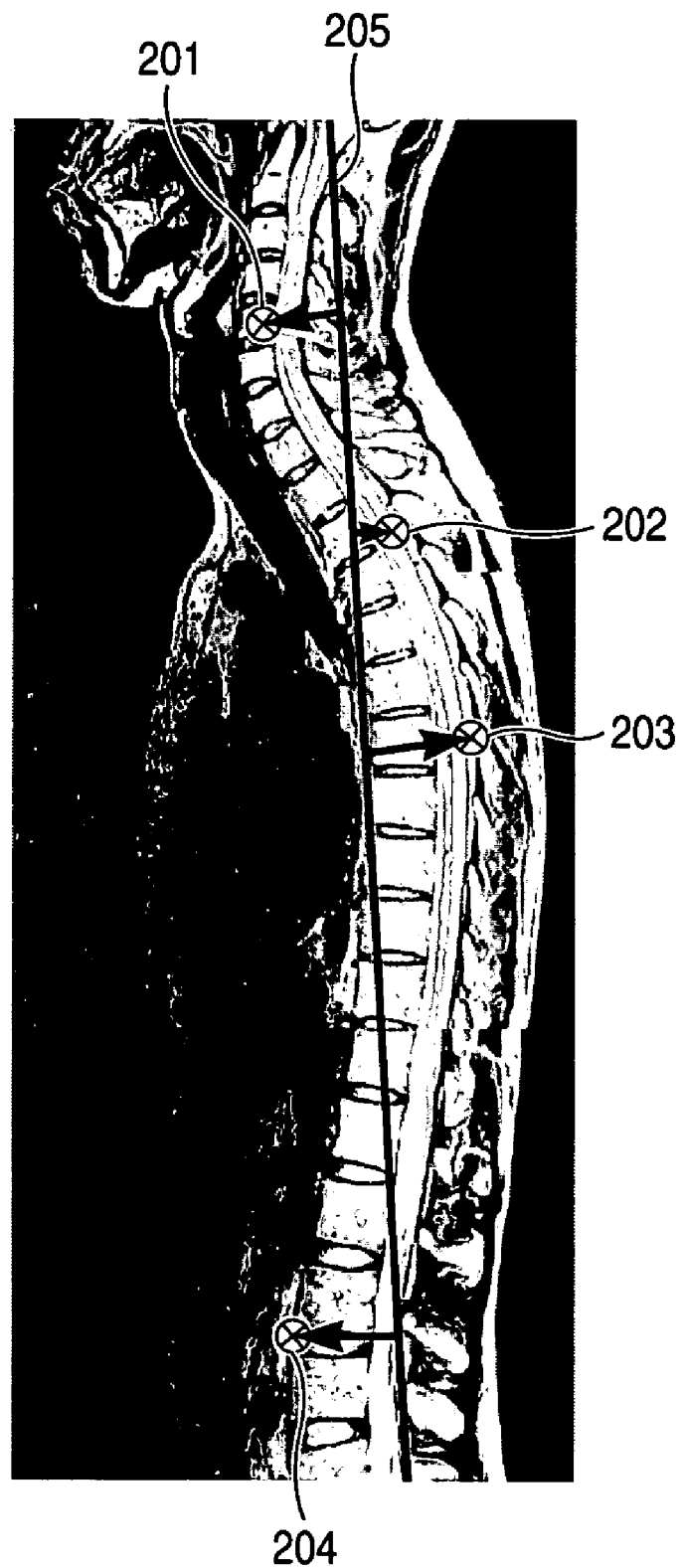
FIG. 6 is a view comparing distances between the approximate line and four regions of interest shown in FIG. 4.

In step Sa4, the control unit 107 calculates the distance from the approximate line for each region of interest and then acquires the greatest distance as the maximum. As for the above example, as shown in FIG. 6, the distance between the region of interest 203 and the approximate line 205 is the maximum distance. In step Sa5, the control unit 107 defines the thickness of coverage required to surround all the regions of interest centered about the approximate line on the basis of the maximum distance. In the simplest way, the thickness of the coverage may be two times the maximum distance. However, in order that the coverage more covers the outside, the thickness is determined by multiplying the maximum distance added by a predetermined value (e.g. thickness of one slice) by 2.

Figure 7:
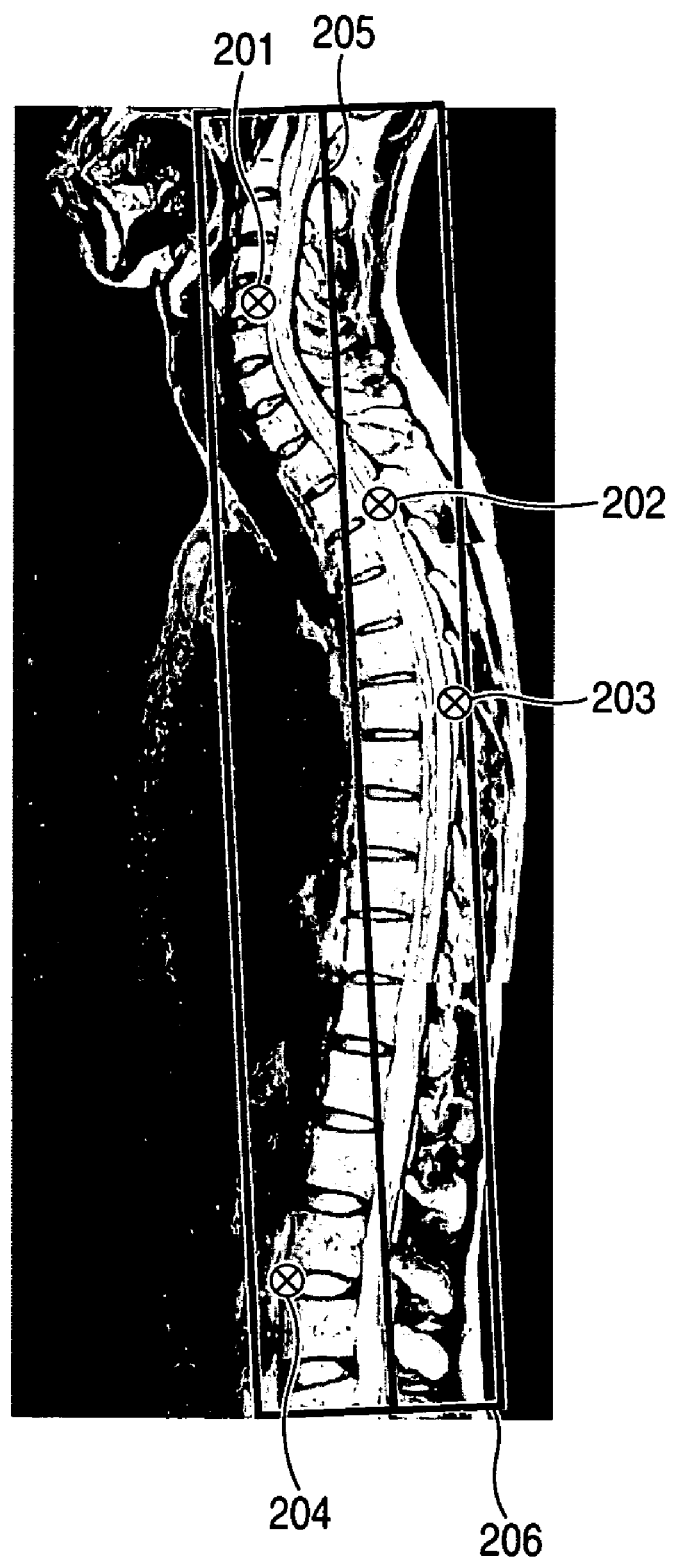
FIG. 7 is a view illustrating coverage defined on the basis of the approximate line and four regions of interest shown in FIG. 4.

In step Sa6, the control unit 107 defines an area having a thickness determined in step Sa5 as a coverage with respect to the approximate line acquired in the step Sa2. FIG. 7 is a view showing coverage 206 defined on the basis of the regions of interest 201 to 204 and the approximate line 205.

In step Sa7, the control unit 107 determines the number of slices on the basis of the slice thickness and slice gap that are set in advance as the thickness and imaging conditions determined in step Sa5. For example, when the coverage thickness is Ct, slice thickness is St, and slice gap is Sw, the number of slices may be obtained from the following equation.

$$\text{number of slices} = \text{Func}A\,((Ct)/(St+Sw))$$

(where, FuncA (x) is the smallest integer that is larger than x).

In step Sa8, the control unit 107 determines a slice center concerning each of several times of imaging to image the whole coverage. Some methods are available for the determination, but two typical methods are described below.

(1) First Method

Figure 8:
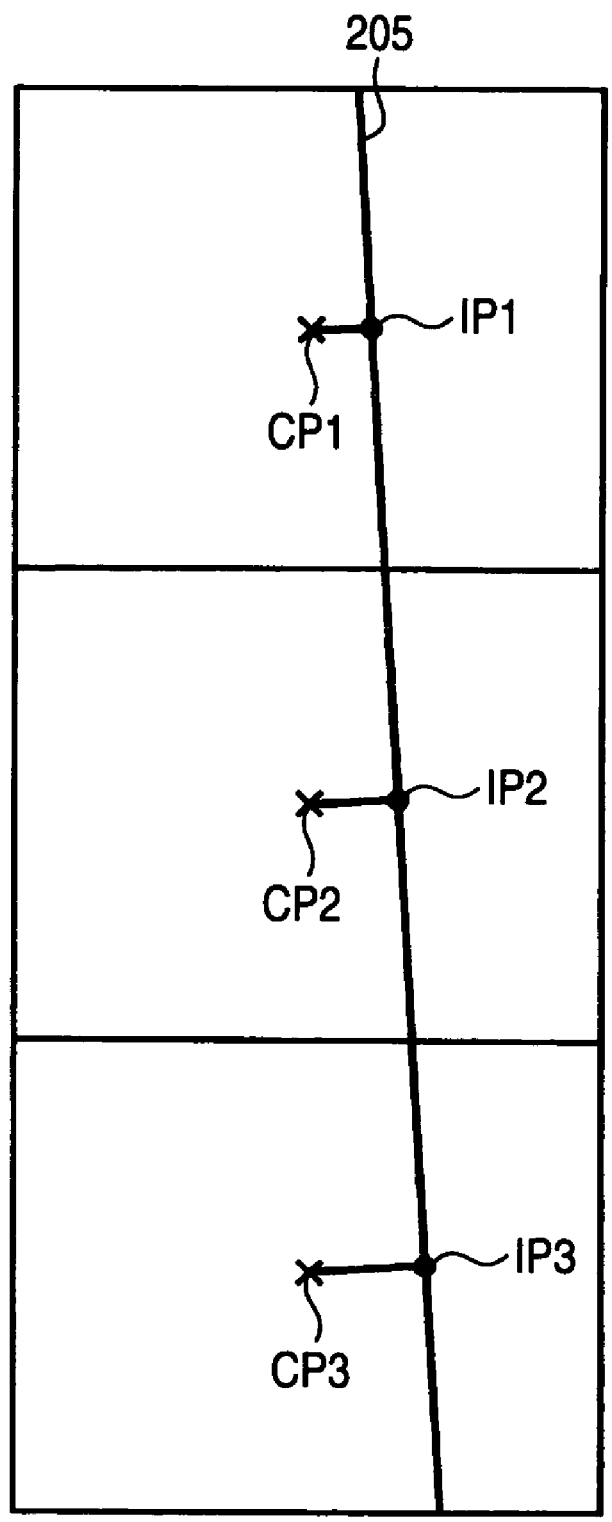
FIG. 8 is a view illustrating a method of determining the centers of slices.

The control unit 107, as shown in FIG. 8, determines intersection points IP1, IP2, IP3 of the approximate line 205 and perpendicular lines from the center points CP1, CP2, CP3 to the approximate line 205. The control unit 107 determines the intersection points IP1, IP2, IP3 as first to third slice centers, respectively. Only the outline of the original images is shown in FIG. 8.

(2) Second Method

The control unit 107 obtains intersection points IP1, IP2, IP3 the same as in the first method. The control unit 107 determines middle points between the intersection points (centers when the weight of all the intersection points is 1) as coverage centers, and then determines the coverage centers and points that moves parallel to the approximate line 205 by a predetermined FOV distance from the coverage centers as slice centers.

In step Sa9, the control unit 107 displays the image conditions such as the above cross-sectional direction, the number of slices, and the slice centers that are determined in the previous steps, for example, on the display 105.

Following step Sa9, in steps Sa10 and Sa11, the control unit 107 is in a stand-by state for an order about change or confirmation of the displayed imaging conditions. For example, when an operator changes the imaging conditions through the input unit 106, the control unit 107 proceeds from the step Sa10 to the step Sa11. The control unit 107 changes the imaging conditions in step Sa11 according to the request of the operator. The control unit 107 then returns to standing by in steps Sa10 and Sa11.

For example, when an operator confirms the imaging conditions through the input unit 106, imaging-plan is completed accordingly, and the control unit 107 finishes the process shown in FIG. 2.

When imaging is processed according to the imaging-plan as described above, a cross section that crosses the original image is imaged in the coverage. If the coverage is larger than a region that can be imaged at one time, the control unit 107 controls the gradient magnetic field power source 3, bed control unit 5, transmitter 7, receiver 9, and data collecting unit 102 to allow several times of imaging by moving the top board 41.

In more detail, the control unit 107 controls each part so that imaging proceeds in the following order.

Figure 9:
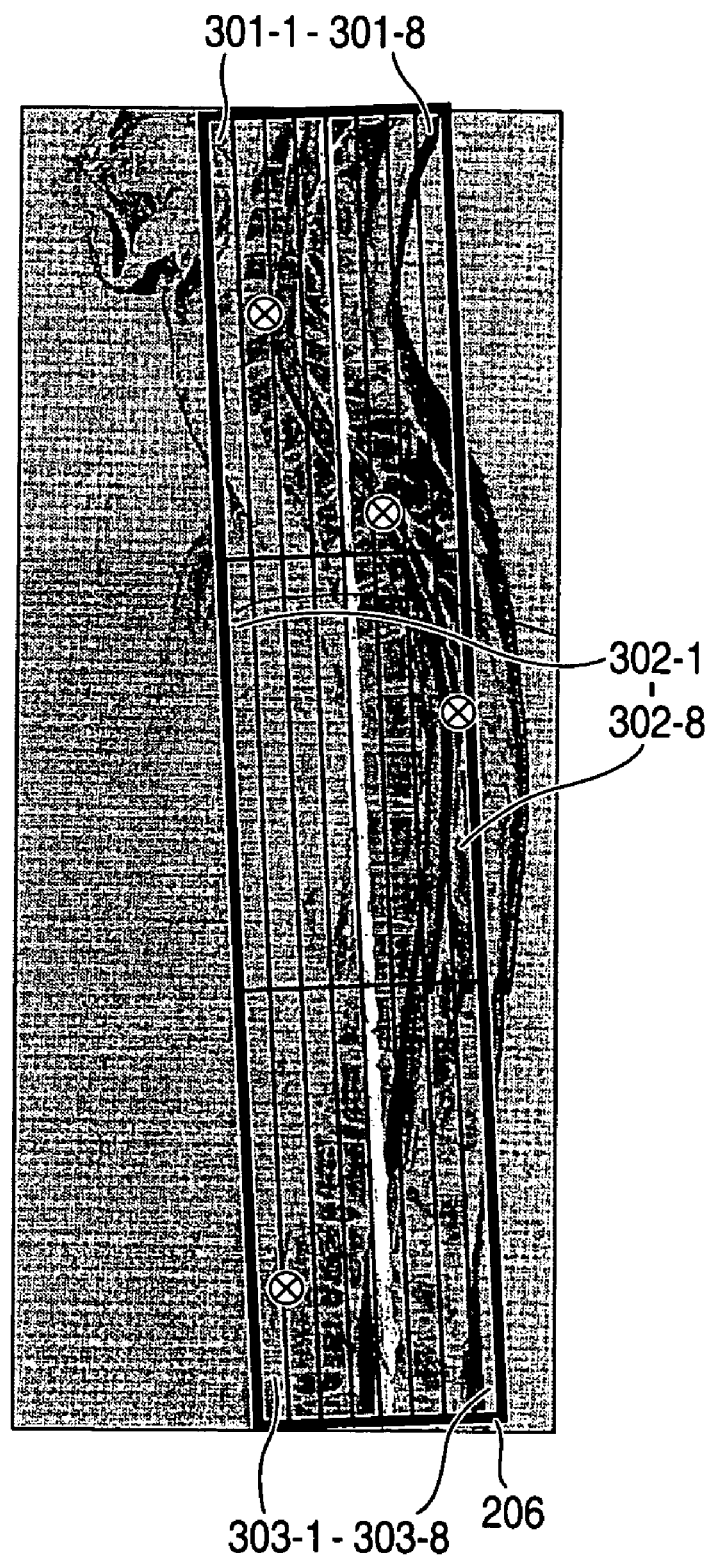
FIG. 9 is a view of an example showing the determined imaging slices.

As for the defined coverage 206 shown in FIG. 7, for example, as shown in FIG. 9, slices 301-1 to 301-8, 302-1 to 302-8, 303-1 to 303-8 are specified, in which imaging is applied to the slices 301-1 to 301-8 first, while the top board 41 is stopped. Subsequently, while the top board 41 is stopped after longitudinally moving at a predetermined distance, imaging is applied to the slices 302-1 to 302-8. Finally, while the top board 41 is stopped after longitudinally moving further at a predetermined distance, imaging is applied to the slices 303-1 to 303-8.

As the imaging is applied, although coverage is larger than the region that can be imaged at one time, the whole region inside the coverage can be imaged.

As described above, according to an MRI apparatus of an embodiment of the invention, because a part of imaging condition involved in imaging of wide area is automatically determined, an operator can easily make an imaging-plan with reference to the automatically determined results.

The above embodiment of the invention can be modified into a variety of ways as follows.

It is preferable to include the thickness of coverage and the coverage in imaging conditions to display. It is not necessarily needed to display cross-sectional direction, the number of slices and slice centers.

It is preferable to determine information other than FOV and disposition of slices as one of the imaging conditions, and it is preferable to display the information accordingly. In particular, when FOV is displayed, it is convenient to display that an adjacent FOV overlaps the above FOV to easily recognize it.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus comprising:
a unit for specifying a plurality of regions of interest on a plurality of original images acquired by imaging several times while changing imaging positions;
a unit for finding an approximate line related to the regions of interest on a composite image formed by combining the original images, said approximate line passing intermediately between said regions of interest; and
a determining unit for determining conditions required to image at least one cross sectional image substantially parallel to said approximate line and encompassing plural of said regions of interest across plural of said original images on the basis of the approximate line.

2. The apparatus according to claim 1,
wherein the determining unit determines a direction of a surface that is formed along the approximate line and crosses the original images as a cross-sectional direction.

3. The apparatus according to claim 1,
wherein the determining unit includes:
a unit for defining coverage surrounding all of the regions of interest centered about the approximate line; and
a unit for determining the number of slices on the basis of the size of coverage and predetermined thickness and gap of the slices.

4. The apparatus according to claim 1,
wherein the determining unit determines a central position of a scan area for one imaging position on the basis of intersecting points of a line passing the center of the original image and the approximate line.

5. The apparatus according to claim 4,
wherein the determining unit determines the intersecting points as central positions of the scan areas.

6. The apparatus according to claim 4,
wherein the determining unit finds two adjacent intermediate points of the intersection points for each of the original image and determines points, which are spaced at a predetermined distance along the approximate line from the central points corresponding to the half of the width of the scan areas, as central points of the scan areas.

7. The apparatus according to claim 1,
wherein the determining unit includes a unit for showing the determined conditions to an operator.

8. The apparatus according to claim 7,
wherein the determining unit further includes a unit for changing the determined conditions according to request of the operator.

9. A magnetic resonance imaging apparatus comprising:
an imaging unit for generating magnetic resonance signals by applying gradient magnetic fields and high frequency pulses to an object in a static magnetic field;
a bed for longitudinally sliding a top board with an object placed;
a high frequency coil for detecting the magnetic resonance signals;
a display unit for displaying positioning images;
a specifying unit for specifying a plurality of regions of interest according to specifying order of an operator on the positioning images;
a calculating unit for calculating coverage surrounding a plurality of regions of interest depending on the regions of interest specified by the specifying unit;
a changing unit for changing the coverage according to changing order of the operator; and
a control unit for controlling the imaging unit, the bed, and the high frequency coils to image cross sections, several times while shifting imaging positions, which is formed by the coverage crossing the positioning image when the coverage defined by confirmation about the conditions of the operator is larger than a region defined by the static magnetic field and can be imaged.

10. The apparatus according to claim 9,
wherein the control unit controls the imaging unit such that the imaging unit images a plurality of cross sections during each of the several times of imaging.

11. A method of making an imaging-plan comprising:
using an MRI system having at least one programmed computer to specify a plurality of regions of interest on a plurality of original images acquired by imaging several times while shifting imaging positions;
find an approximate line related to the regions of interest on a composite of the original images, said approximate line passing intermediately between said regions of interest; and
determine conditions for imaging at least one cross sectional image substantially parallel to said approximate line and encompassing plural of said regions of interest across plural of said original images on the basis of the approximate line.

12. The method according to claim 11,
wherein a surface that is formed along the approximate line and crosses the original images is determined as a cross-sectional direction in the conditions.

13. The method according to claim 11, further comprising:
defining coverage surrounding all of the regions of interest centered about the approximate line; and
determining the number of slices as the conditions on the basis of the size of the coverage, predetermined thickness and gap of the slices.

14. The method according to claim 11, further comprising:
determining a central position of a scan area for one imaging as the conditions on the basis of intersecting points of a line passing the center of the original image and the approximate line.

15. The method according to claim 14, further comprising:
determining the intersecting points as central positions of the scan areas.

16. The method according to claim 14, further comprising:
finding two adjacent intermediate points of the intersection points for each of the original image; and
determining points, which are spaced at a predetermined distance along the approximate line from the central points corresponding to the half of the width of the scan areas, as central points of the scan areas.

17. The method according to claim 11, further comprising:
showing the determined conditions to an operator.

18. The method according to claim 17, changing the determined conditions according to the request of the operator.

19. A method of imaging using a magnetic resonance imaging apparatus that includes an imaging unit for generating magnetic resonance signals by applying gradient magnetic fields and high frequency pulses to an object in a static magnetic field, a bed for longitudinally sliding a top board while an object is placed, a high frequency coil for detecting the magnetic resonance signals, and a display unit for displaying positioning images; the method comprising:

specifying a plurality of regions of interest according to specifying order of an operator on the positioning images; calculating coverage surrounding a plurality of regions of interest depending on the regions of interest specified by the specifying unit; changing the coverage according to changing order of the operator; and controlling the imaging unit, the bed, and the high frequency coil so as to image cross sections of the coverage several times while shifting imaging positions that crosses the positioning image when the coverage defined by confirmation about the conditions of the operator is larger than an image allowable region defined by the static magnetic field.

20. The method according to claim 19, further comprising:
imaging a plurality of cross sections for each of the several times of imaging.

* * * * *